US009726643B2

(12) United States Patent
Comeaux et al.

(10) Patent No.: US 9,726,643 B2
(45) Date of Patent: Aug. 8, 2017

(54) GATE VALVE REAL TIME HEALTH MONITORING SYSTEM, APPARATUS, PROGRAM CODE AND RELATED METHODS

(71) Applicant: Vetco Gray Inc., Houston, TX (US)

(72) Inventors: David Daniel Comeaux, Houston, TX (US); Gangbing Song, Pearland, TX (US); Jiabiao Ruan, Houston, TX (US); Dhaval Mistry, Houston, TX (US); Mahesha Udipi, Houston, TX (US)

(73) Assignee: Vetco Gray Inc., Houston, TX (US)

( * ) Notice: Subject to any disclaimer, the term of this patent is extended or adjusted under 35 U.S.C. 154(b) by 605 days.

(21) Appl. No.: 14/141,205

(22) Filed: Dec. 26, 2013

(65) Prior Publication Data
US 2014/0182381 A1 Jul. 3, 2014

Related U.S. Application Data

(60) Provisional application No. 61/746,693, filed on Dec. 28, 2012.

(51) Int. Cl.
*G01N 29/14* (2006.01)
*G01M 3/00* (2006.01)
(Continued)

(52) U.S. Cl.
CPC ............. *G01N 29/14* (2013.01); *F16K 3/02* (2013.01); *F16K 37/0075* (2013.01);
(Continued)

(58) Field of Classification Search
CPC ........ G01N 29/14; G01N 29/12; G01N 29/02; G01N 2291/044; G01N 2291/022;
(Continued)

(56) References Cited

U.S. PATENT DOCUMENTS 4,805,451 A 2/1989 Leon
4,882,937 A * 11/1989 Leon ................ G01B 7/16
  73/168

(Continued)

FOREIGN PATENT DOCUMENTS

AU  2011213746 A1  3/2012
DE  102008059712 A1  6/2010
(Continued)

OTHER PUBLICATIONS

Tamutus, Terry, et al., "Valve Leak Quantification with Acoustic Emission," The American Society for Nondestructive Testing, the NDT Technician, Apr. 10, 2010, pp. 2-6, vol. 9, No. 2.

(Continued)

*Primary Examiner* — Laura Martin
*Assistant Examiner* — Rose M Miller
(74) *Attorney, Agent, or Firm* — Hogan Lovells US LLP

(57) ABSTRACT

Systems, apparatus, and program code, and methods for monitoring the health and other conditions of the valve, are provided. An exemplary system for monitoring the condition of the gate valve includes a logic module configured to perform the operations of receiving sensor data providing an acoustic emission, vibration, and/or stream level signature and determining the level of lubricity, level of friction, level of surface degradation, and leakage rate at a gate-valve seat interface. An exemplary method for monitoring the condition of the gate valve includes receiving sensor data providing an acoustic emission, vibration, and/or stream level signature and determining the level of lubricity, level of friction, level of surface degradation, and leakage rate at a gate-valve seat interface.

23 Claims, 11 Drawing Sheets

(51) Int. Cl.
*F16K 37/00* (2006.01)
*F16K 3/02* (2006.01)
*G01N 29/12* (2006.01)
*G05B 23/02* (2006.01)

(52) U.S. Cl.
CPC .............. *G01M 3/00* (2013.01); *G01N 29/12* (2013.01); *G05B 23/0245* (2013.01); *G01N 2291/269* (2013.01); *G05B 2219/24042* (2013.01); *G05B 2219/37274* (2013.01); *G05B 2219/37337* (2013.01); *G05B 2219/37351* (2013.01); *G05B 2219/45006* (2013.01)

(58) Field of Classification Search
CPC .... G01N 2291/269; G01N 13/00; F16K 3/02; F16K 37/0091; F16K 37/0083; F16K 51/00; Y10T 137/8158; G01M 3/00; G05B 23/0245; G05B 2219/24042; G05B 2219/37274; G05B 2219/37337; G05B 2219/37351; G05B 2219/45006
USPC .......................................... 73/587, 592, 593
See application file for complete search history.

(56) References Cited

U.S. PATENT DOCUMENTS

| | | | | |
|---|---|---|---|---|
| 4,896,101 | A * | 1/1990 | Cobb | F16K 37/0083 |
| | | | | 324/73.1 |
| 5,115,672 | A * | 5/1992 | McShane | G01F 1/7082 |
| | | | | 137/554 |
| 5,257,545 | A * | 11/1993 | Au-Yang | F16K 37/00 |
| | | | | 367/99 |
| 5,433,245 | A | 7/1995 | Prather et al. | |
| 5,594,175 | A | 1/1997 | Lyon et al. | |
| 5,616,829 | A * | 4/1997 | Balaschak | F16K 31/046 |
| | | | | 137/551 |
| 7,318,350 | B2 | 1/2008 | Boken | |
| 2003/0019297 | A1 | 1/2003 | Fiebelkorn et al. | |
| 2004/0128109 | A1 | 7/2004 | Saito et al. | |
| 2007/0068225 | A1 * | 3/2007 | Brown | F16K 37/0075 |
| | | | | 73/40.5 A |
| 2007/0185659 | A1 * | 8/2007 | Love | G01N 30/88 |
| | | | | 702/35 |
| 2012/0051186 | A1 | 3/2012 | Holley | |
| 2012/0274333 | A1 | 11/2012 | Anderson | |

FOREIGN PATENT DOCUMENTS

| | | |
|---|---|---|
| EP | 2423429 A1 | 2/2012 |
| GB | 2282434 A | 4/1995 |

OTHER PUBLICATIONS

AV Technology, "'Machines Talk and it Pays to Listen'," Acoustic Emission Technology, Apr. 28, 2012.
GE Oil & Gas, "Acoustic Emission System for Cylinder Valve Monitoring," Dec. 31, 2008.
PCT Search Report and Written Opinion issued Apr. 11, 2014 in connection with corresponding PCT Patent Application No. PCT/US2013/078017.
European Office Action mailed Feb. 3, 2017 in corresponding European Patent Application No. 13 821 623.9-1751.

* cited by examiner

GATE VALVE REAL TIME HEALTH MONITORING SYSTEM, APPARATUS, PROGRAM CODE AND RELATED METHODS

RELATED APPLICATIONS

The present application is a non-provisional of and claims priority to and the benefit of U.S. Provisional Patent Application No. 61/746,693, titled Gate Valve Time Health Monitoring System, Apparatus, Program Code, and Related Methods, filed on Dec. 28, 2012, each incorporated herein by reference in its entirety.

BACKGROUND OF THE INVENTION

1. Field of the Invention

The present invention generally relates to systems, apparatus, program code, computer readable medium, and methods for performing real-time health monitoring of valves, and more particularly, for performing real-time health monitoring of gate and other similar types of valves.

2. Description of the Related Art

A valve is a device that is configured to regulate the flow of fluids. The regulation of fluid flow is facilitated by the opening and closing of the valve. Gate valves are widely used in the oil industry for gas transportation. Typically, a gate valve includes a controlled gate that moves up or down against valve seats to permit or prevent the flow of fluid through the gate valve.

The working environment for a gate valve can be challenging due to the high pressure and temperature of fluid flow. Specifically, due to the compressive forces, the surfaces of the gates and valve seats tend to wear and tear, which may result in large actuating forces, incomplete closing of the valve, and loss of internal sealability.

Current techniques to monitor the health of a gate valve require regular service times and experienced technicians. While the valve health is being verified by the technician, the entire pipe line is typically shut down, even for maintenance of a single valve. The time required to check the valve health is often long, and the effectiveness of the check itself is dependent on the experience of the technician. In other words, current maintenance techniques incur significant costs due to the need to shut down the pipeline and to the expense of the manpower to perform the maintenance.

In the field of pipeline leak detection, acoustic sensors have been used to detect holes in the pipeline. An acoustic sensor positioned outside the pipeline can record noise of fluid within the pipeline to establish an acoustic fingerprint, and can detect a low-frequency acoustic sound created by liquid escaping through a hole in the pipe.

In the field of reciprocating compressors, and more specifically, in the field of intake and discharge valves utilized in reciprocating compressors, it has been proposed that through utilization of acoustic emission sensors and by graphically plotting vibrations as a function of crank angle, the graphs can be analyzed and compared to predetermined baseline signatures of a corresponding intake or discharge valve that is working to detect large deviations from the baseline. It has been asserted that these deviations can provide early detection of a leaking valve, valve slamming (valve tap), stiff or weak valve springs, and valve stiction.

SUMMARY OF THE INVENTION

Recognized by the inventors, however, is that gate valves and other types of sliding valves such as ball valves involve moving components under substantial pressures when opening and closing, which would require different sensor placement techniques and which would require construction of acoustic emission, vibration, and/or strain signature models unique to such type of valves. For example, a gate valve has at least two, but more typically four sealing surfaces, one being the face of each valve seat, and the other being the upstream and downstream sides of the body of the gate. The upstream side of the gate is in fluid contact with a pressurized fluid. This causes a significant surface-surface contact force between the gate-valve seat interface on the downstream side. Movement of the body of the gate across the surfaces of the valve seat generally occur while the gate is being subjected to a compressive force caused by fluid flowing in a direction substantially normal to the direction of slidable movement.

In view of the foregoing, various embodiments of the present invention advantageously provide apparatus, computer program, and methods for monitoring a condition of a gate or other similar type of valve to provide real-time health data, eliminating or reducing downtime and human intervention, and allowing continuous automated monitoring and maintenance scheduling, thus eliminating problems associated with prior systems for monitoring gate valves.

For example, an exemplary method for monitoring a condition of a gate valve, the gate valve includes positioning sensors adjacent to or in contact with an outer surface of the housing of the gate valve. The sensors can include acoustic emission, vibration, and/or strain level sensing sensors. The vibration and strain level sensors can be in the form of PZT or other solid-state sensors. The sensors can be connected to or positioned adjacent an outer surface of the housing of the gate valve, within a cavity containing the gate, and/or on a gate, itself. The method can also include receiving sensor data including an acoustic emission, vibration and/or strain level signature representing one or more characteristics of an interface between surface portions of the gate body and surface portions of the valve seats ("gate-valve seat interface"). The characteristics which can be extracted from the sensor signal data includes the level of lubricity, level of friction, level of surface degradation, and/or leakage rate at the gate-valve seat interfaces. Additionally, a temperature probe can provide temperature signals as the data signal provided by the sensors can vary depending upon the temperature, all other factors remaining the same.

In a passive sensing mode, the sensor signals can be acoustic emissions and vibrations as a result of slidable engagement of outer surface portions of the gate across surface portions of the valve seats. In an active sensing system mode, the sensor signal can be the result of the sensors detecting reflected or refracted portions of an ultrasonic wave created by an actuator connected to a component of the gate valve. In the active sensing system mode, the gate can remain in a stationary position in surface contact with the valve seats. The active and passive sensing system modes can be employed separately or in combination to provide additional information regarding the health or other characteristic of the gate valve.

According to this exemplary method, a data acquisition and analysis system receives the sensor data and compares characteristics of the received data with baseline signature data models associated with different levels of lubrication, friction, degradation, and leakage rate. If any of the determined conditions exceed predetermined levels, an alert or warning can be transmitted for immediate action. If the conditions are less critical, the data can be transmitted to a maintenance module/display for scheduled maintenance.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Various embodiments of the present invention advantageously provide systems, apparatus, computer program code, and methods for monitoring a condition of a gate or other similar type of valve to provide real-time health data, eliminating or reducing downtime and human intervention, and allowing continuous automated monitoring and maintenance scheduling, thus eliminating problems associated with prior systems for monitoring gate valves. Various embodiments can determine or identify the condition of the gate-valve seat interface, with or without lubricant, such as when the surfaces are composed of low friction materials. Various embodiments can detect leakage rates, lubrication quality, surface friction, and/or surface degradation. For example, changes in the characteristics between the gate and valve seat of a gate valve result in changes in the acoustic characteristics during relative movement therebetween when using passive detection and acoustic characteristics of reflected and refracted waves when active detection is utilized. Various embodiments can include provisions for calibrating reference signatures, or values extracted from reference signatures, which are gate and/or valve seat material dependent. Various embodiments can also include provisions for remote monitoring of multiple valves simultaneously, in real-time.

Figure 1:
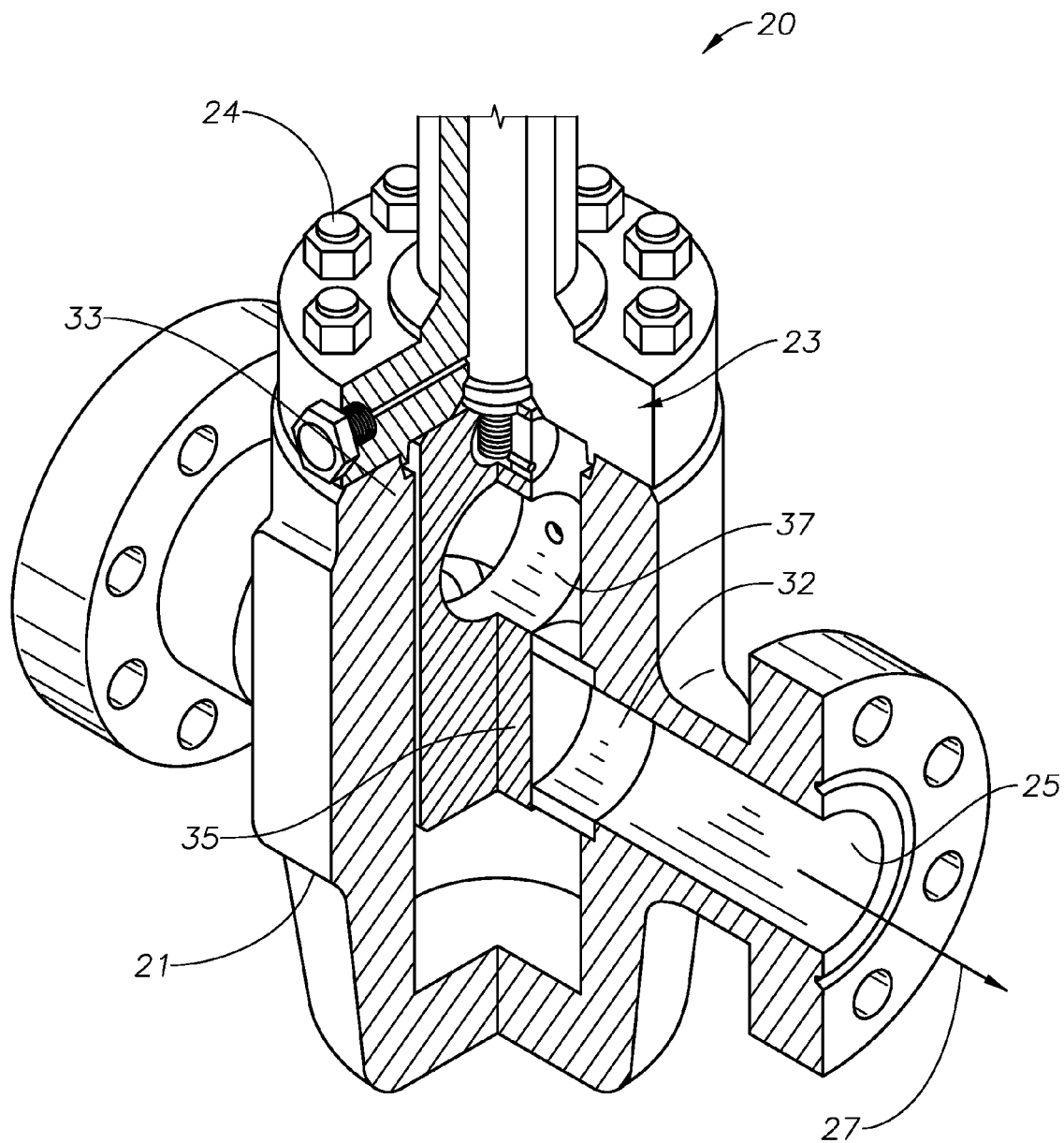
FIG. 1 is partially perspective, partially cutaway view of an embodiment of a gate valve shown with the gate in a closed position.

FIG. 1 shows a gate valve 20 comprising a valve housing 21 and a cap 23 that are joined with bolts 24 and sealed to each other. The housing 21 has a fluid pathway 25 that extends through the housing 21 along a fluid axis 27. A pair of valve seats 31, 32 (see FIG. 2) are mounted in the housing 21 along the fluid axis 27. The valve seats 31, 32, are located on opposite sides of a gate 33. The gate 33 is movably mounted within the housing 21 along a valve axis between the valve seats 31, 32. The gate 33 has two sealing surfaces for engaging respective sealing surfaces of the valve seats 31, 32, to form metal-to-metal seals. The valve seats 31, 32, can include seal rings (not shown).

The exemplary gate 33 also includes a fluid blocking body portion 35 and a fluid transmission aperture 37 extending through the body of the gate 33. The gate 33 is movable between an open position that aligns the aperture 37 with the fluid pathway 25 and valve seats 31, 32, to permit fluid flow, and a closed position that positions the aperture 37 so that the aperture 37 is not aligned with fluid pathway 25 and valve seats 31, 32, to prevent fluid flow. The gate 33 and valve seats 31, 32, are typically greased to improve the seal formed between the gate 33 and valve seats 31, 32 (a.k.a. gate-valve interface), and to prevent excessive wear. During the service life of the gate valve 20, friction between the gate 33 and valve seats 31, 32, causes wear and tear, which necessitates maintenance of the gate valve 20.

Figure 2:
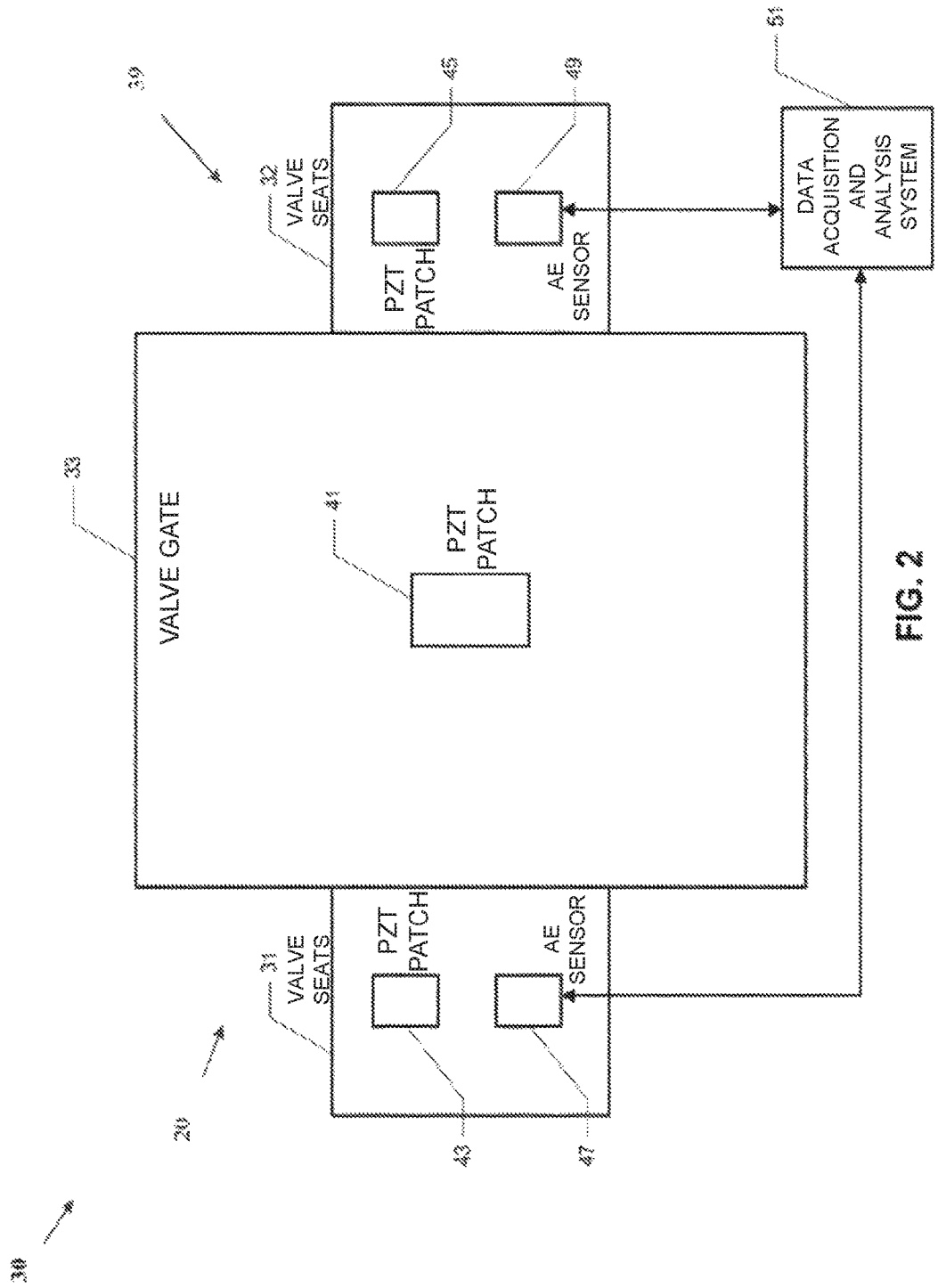
FIG. 2 is a schematic diagram of a gate valve and a health monitoring system according to an embodiment of the present invention.

FIG. 2 shows a gate valve 20 with an integrated sensing system 39 of a health monitoring system 30, according to one embodiment of the present invention. The gate valve 20 shown in FIG. 2 may be substantially similar to the gate valve 20 discussed above with respect to FIG. 1 except for the differences discussed below.

Figure 3:
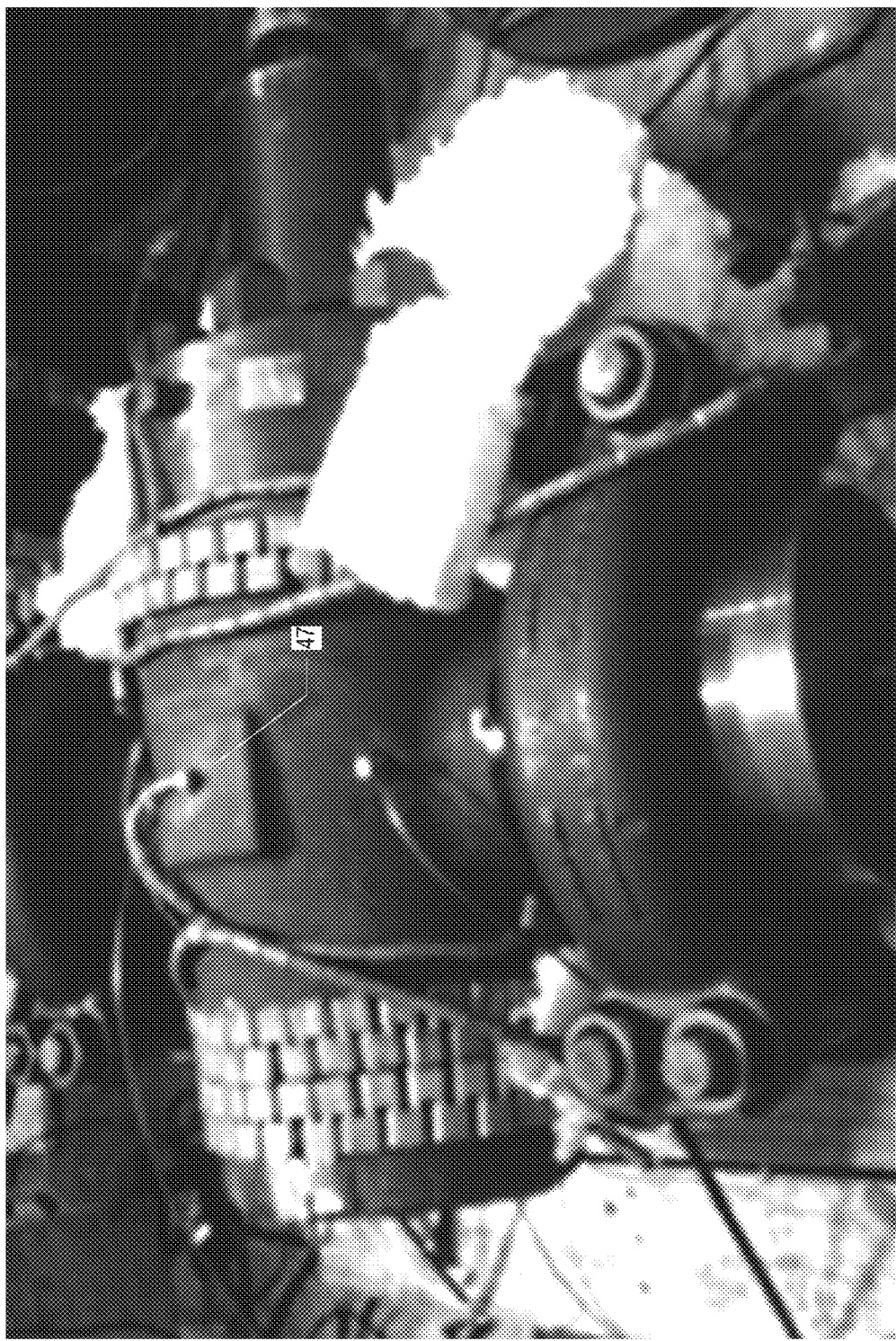
FIG. 3 is a perspective view of a gate valve and portion of a health monitoring system according to an embodiment of the present invention.

FIG. 3 shows a gate valve 20 with an external acoustic emission "AE" sensor 47. In this example, the AE sensor 47 is attached to the exterior surface of the gate valve 20, allowing for the measurements to be obtained without alteration of the gate valve 20. I.e., the external installation of the AE sensor 47 allows for the present invention to be installed in existing gate valve systems. As would be understood by one of ordinary skill in the art, an alternative type of sensor such as, for example, a lead-zirconate-titanate (PZT) sensor could also or alternatively be so installed.

In other embodiments, internal AE sensors, PZT sensors, or less desirable alternative forms, can be used to obtain data measurements from the gate valve 20. In this case, the gate valve 20 can be modified to accommodate the sensors at various locations such as, but not limited to, a surface of the valve gate 33 and a surface of the valve seats 31, 32.

Referring again to FIG. 2, according to the illustrated embodiment, a PZT patch 41 connected to or adjacent the valve gate 33, can be used as an actuator or sensor. In some embodiments, one or more PZT patches 43, 45, can be connected to one or more of the valve seats 31, 32. Each of the PZT patches 41, 43, 45 can correspond to a PZT sensor or actuator that can be interchanged with one another. In other words, each PZT sensor 41, 43, 45, can work as a PZT actuator and vice versa.

In some embodiments, PZT can be used to make ultrasound transducers, vibration sensors, strain level sensors, or other sensors and actuators corresponding to the PZT patches 41, 43, 45. If the gate valve 20 is configured in an active sensing mode, one or more of the PZT patches 41, 43, 45 (e.g., patch 41) function as a PZT actuator that is configured to generate ultrasonic waves at a particular frequency. In this case, the gate valve 20 may also include PZT sensors 43, 45, and/or AE sensors 47, 49, to receive the ultrasonic waves generated by the PZT patch or patches 41, 43, 45. If the gate valve 20 is configured in a passive sensing mode, the PZT patches 41, 43, 45, function as PZT sensors 41, 43, 45, that are configured to receive a wave signal as the valve gate 33 moves up and down between the valve seats 31, 32.

An abnormal acoustic signal can be received by the PZT patches 41, 43, 45, or AE sensors 47, 49, when surface damage of the valve gate 33 or the valve seats 31, 32, occurs or there is a leakage between the seal formed by the valve gate 33 and the valve seats 31, 32.

The integrated sensing system 39 also provides a data acquisition and analysis system 51 configured to process data received from the AE sensors 47, 49. In some embodiments, the data acquisition and analysis system 51 can also or alternatively be configured to process data received from PZT sensors 41, 43, 45. Processing can be through an analysis of various aspects of the received signal to include signal peak amplitudes, counts, and friction torque RMS values. For example, the two-norm of the AE signal peak amplitudes can represent AE activity energy and the torque RMS value can stand for torque level.

The data acquisition and analysis system 51 can include or be in the form of a logic module such as, for example, a PLC, itself including or having access to a database (not shown) including sets of acoustic emission, vibration, and strain signatures at different lubrication levels, friction levels, degradation levels, and leakage rates for different materials used to form the valve seats 31, 32 and gate 33. These data sets which can provide lubrication level signature models, friction level signature models, degradation level signature models, and leakage rate signature models, form a continuum of signatures/signature models, which can be used to identify the present status of the gate valve 20, in real-time.

The data acquisition and analysis system 51 can enable staff on duty to know the status of the gate valve 20 based on measurements obtained from the AE sensors 47, 49 and/or one or more of the PZT sensors 41, 43, 45. For example, according to an exemplary configuration, the data acquisition and analysis system 51 can be configured to monitor the measurements obtained from the AE sensors 47, 49 for an abnormal acoustic signal. The data acquisition and analysis system 51 can also be configured to present a notification to a user of the abnormal acoustic signal, thereby notifying the user of a potential failure in the gate valve 20.

According to an embodiment, the data acquisition and analysis system 51 is configured to communicate with the AE sensors 47, 49 via electromagnetic, e.g., RF, signals, for example. In this embodiment, the AE sensors 47, 49, can be equipped with transmitters, e.g. RF transmitters, configured to transmit data measurements to an RF receiver (not shown) for/of the data acquisition and analysis system 51, or can be stand-alone RF transmitters (not shown) positioned typically adjacent AE sensors 47, 49, and communication therewith. The RF transmitters can be in communication with the PZT patches 41, 43, 45, to provide actuating signals and/or receive measurement signals.

Those skilled in the art will appreciate that other communication mediums could also be used to communicate data between the data acquisition and analysis system 51 and the transmitters, to include optical transmission or combination with other forms as understood by those of ordinary skill in the art. Those of ordinary skill in the art will also appreciate that in embodiments not including AE sensors 47, 49, or in embodiments where the transmitters are standalone, the transmitters (conceptually shown at 47, 49) can be located either that were shown, but generally in close vicinity with the PZT patches 41, 43, 45 and/or AI sensors 47, 49.

The AE sensors 47, 49 can also include or house a temperature sensor (not shown) to provide temperature data and/or pressure sensor.

According to an embodiment, a logic module of or forming the data acquisition and analysis system 51 can also include memory storing program code and one or more processors. The program code can include instructions that when executed by the one or more processors cause the logic module to perform the data analysis and communication functions described above.

Figure 4:
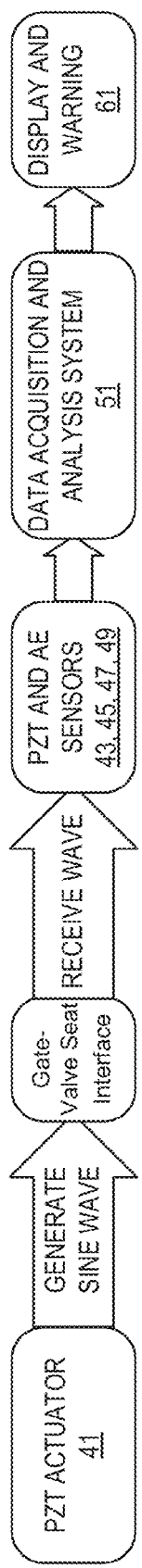
FIG. 4 is a block flow diagram illustrating signal-data flow in an active sensing system according to an embodiment of the present invention.

FIG. 4 illustrates a flow diagram of signal data in an active sensing system configuration. As illustrated in the figure, a PZT actuator 41 initiates a sine wave at a certain frequency or a sweep across a set of frequencies which is imparted to the gate-valve seat interface. Reflected or refracted portions of the generated sign wave are then received by PZT sensors 43, 45, and/or acoustic emission sensors 47, 49. The sensed signal or signals are then forwarded to the data acquisition and analysis system 51, which determines the status of the gate-valve interface. A display and warning system 61 provides a graphical indication of the status and an alert function provides alerts when the status indicates maintenance is required, degradation exceeds preselected limits or imminent failure is anticipated, or leakage exceeds acceptable limits, among others.

Figure 5:
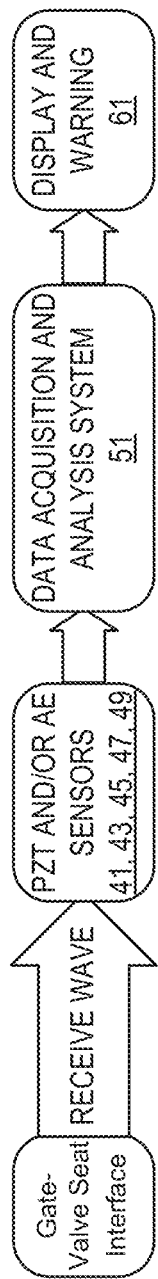
FIG. 5 is a block flow diagram illustrating signal-data flow in a passive sensing system according to an embodiment of the present invention.

FIG. 5 illustrates a flow diagram of signal data in a passive sensing system configuration. As illustrated in the figure, during movement of the gate 33, acoustic emissions and vibrations are generated as a result of slidable movement of the gate 33 across the surfaces of the valve seats 31, 32. These acoustic emissions and vibrations are then received by PZT sensors 43, 45, and/or acoustic emission sensors 47, 49. The sensed signal or signals are then forwarded to the data acquisition and analysis system 51, which as with the active system configuration, determines the status of the data-valve interface. The display and warning system 61 then provides a graphical indication of the status and an alert function provides alerts.

Figure 6:
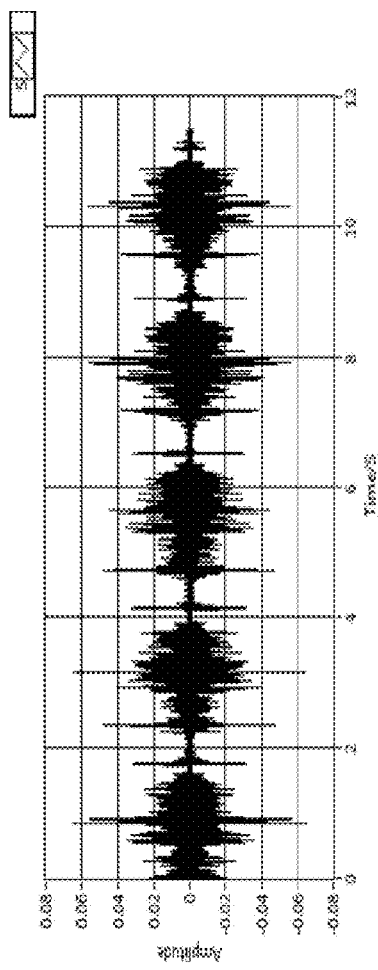
FIGS. 6-17 are graphical illustrations of exemplary acoustic signatures and frequency responses obtained using the workflows shown in FIGS. 4-5 according to an embodiment of the present invention.
Figure 7:
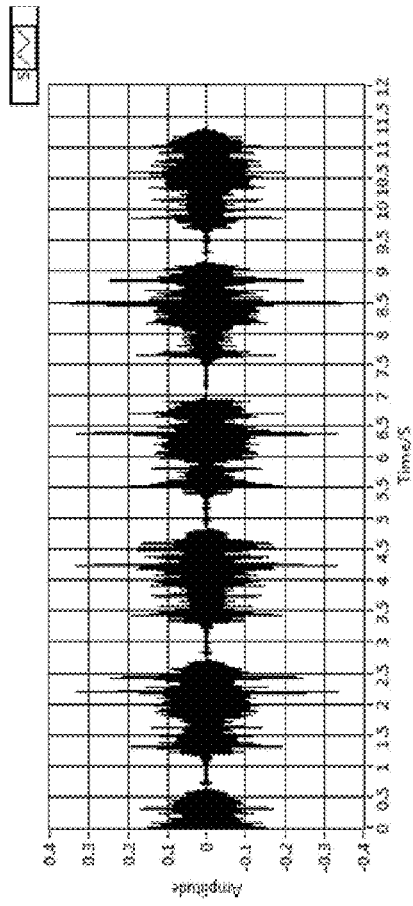
Figure 8:
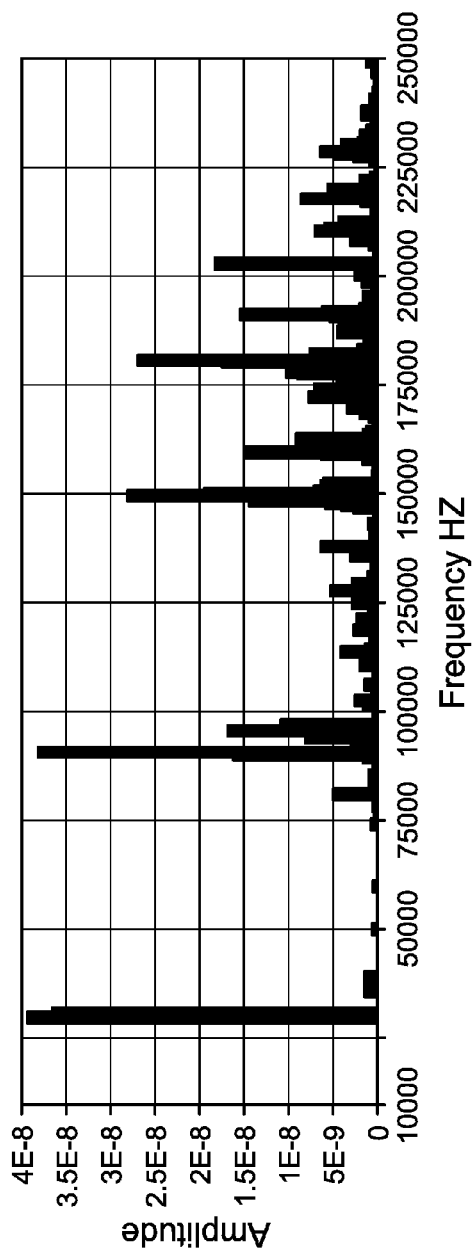
Figure 9:
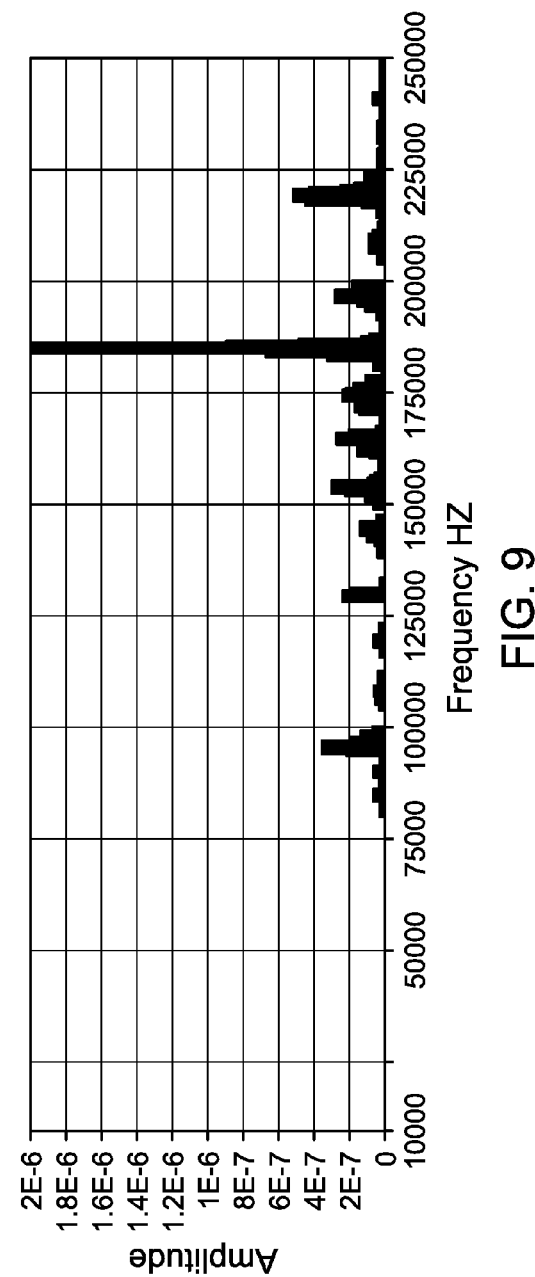

FIGS. 6-19 are graphical illustrations of exemplary acoustic signatures and frequency responses obtained using the workflows shown in FIGS. 4-5 according to one or more embodiments of the present invention. FIGS. 6-7 illustrate a system response to a sweep sine input signal from 10 kHz to 250 kHz produced by a PZT actuator 41. In FIG. 6, the gate-valve seat interface is without grease. In FIG. 7, the gate-valve seat interface is with grease. FIGS. 8 and 9 illustrate the power spectrum plots of the signals shown in FIGS. 6-7, respectively. The with grease condition, provides higher peak values and a broader response.

Figure 10:
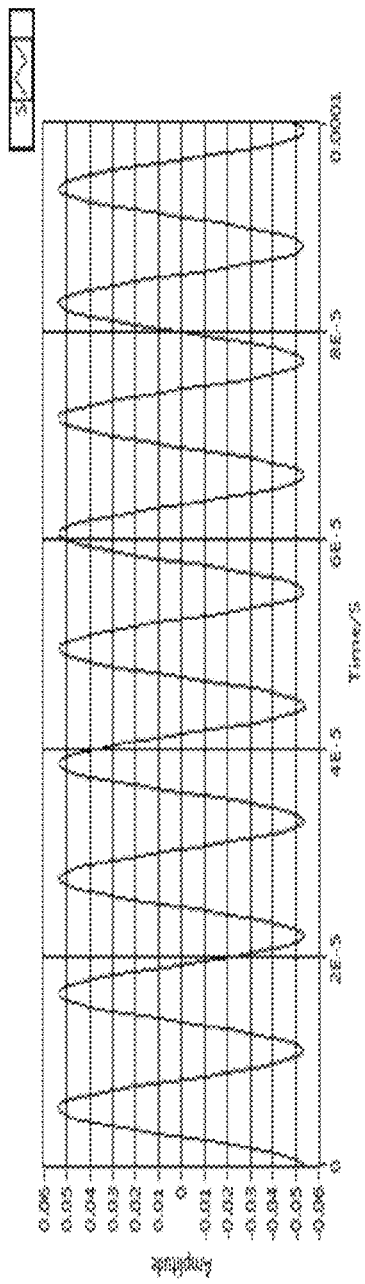
Figure 11:
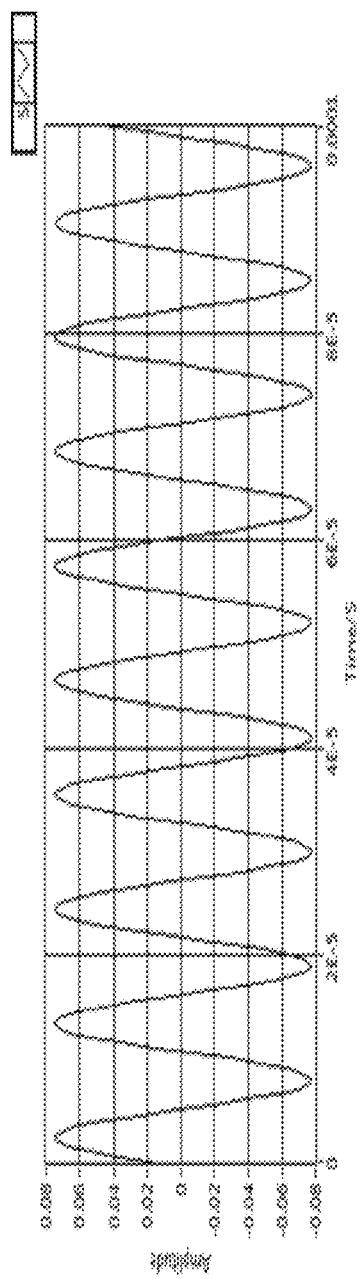
Figure 12:
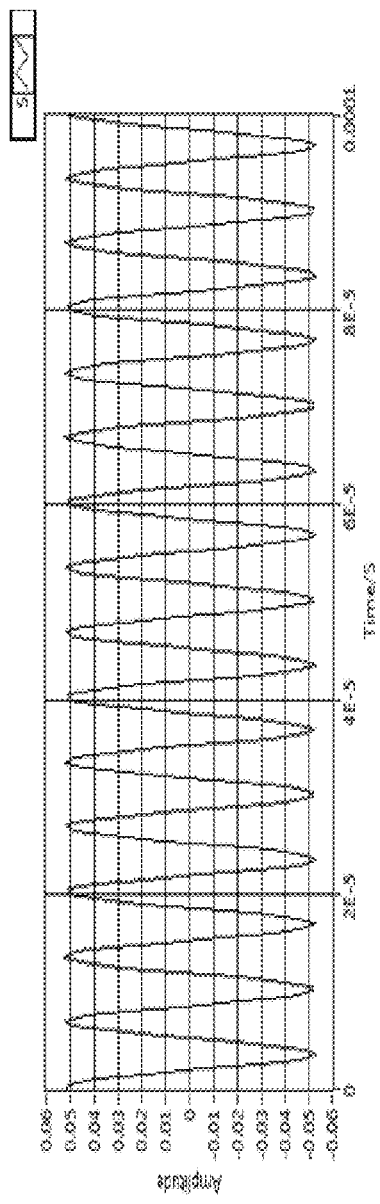
Figure 13:
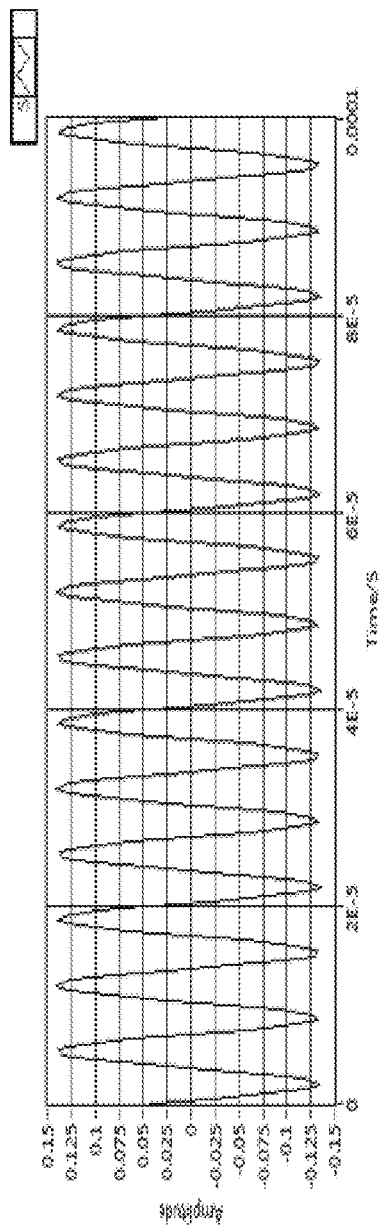

FIGS. 10-11 illustrate system responses to an input sine wave provided by actuator 41 at a frequency of 90.49 kHz for with and without grease conditions, respectively. Similarly, FIGS. 12-13 illustrate system responses to an input sine wave provided by actuator 41 but at a frequency of 149.90 kHz for with and without grease conditions, respectively. Notably, the peak-peak values in the without grease conditions were the same at both frequencies. However, the peak-peak values with grease were higher than without grease at both frequencies, and much higher at the higher frequency.

Figure 14:
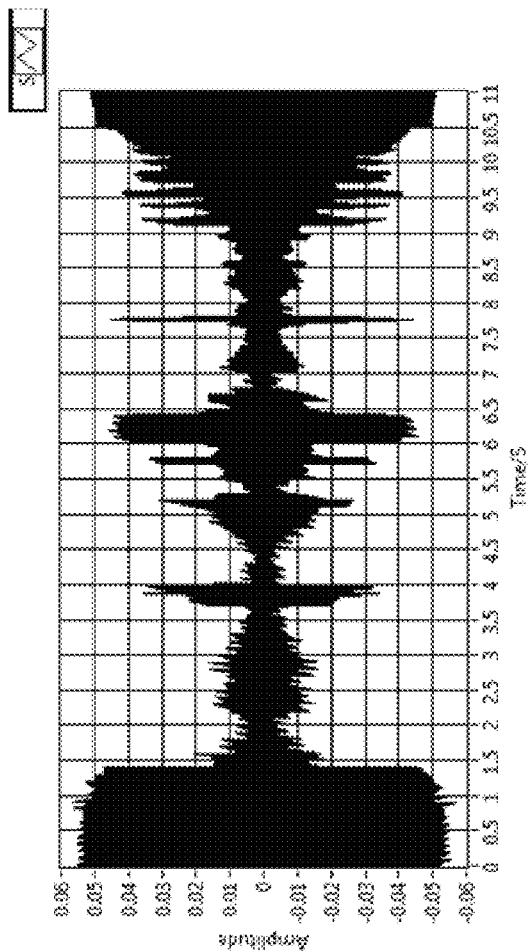
Figure 15:
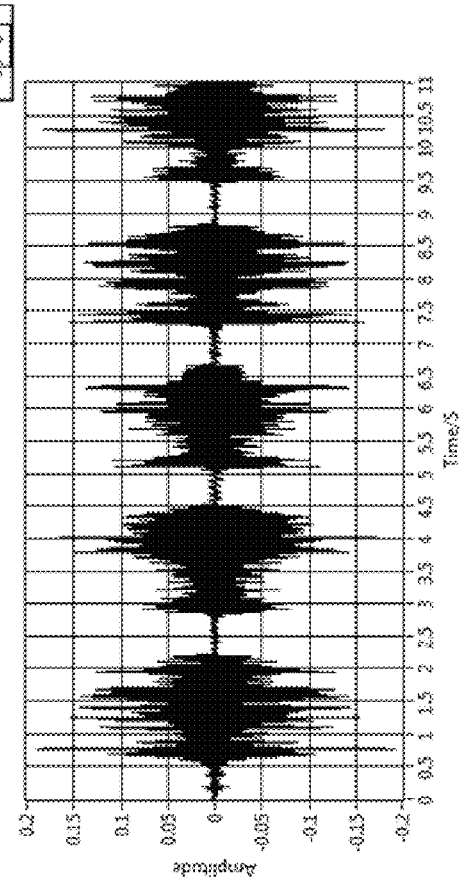
Figure 16:
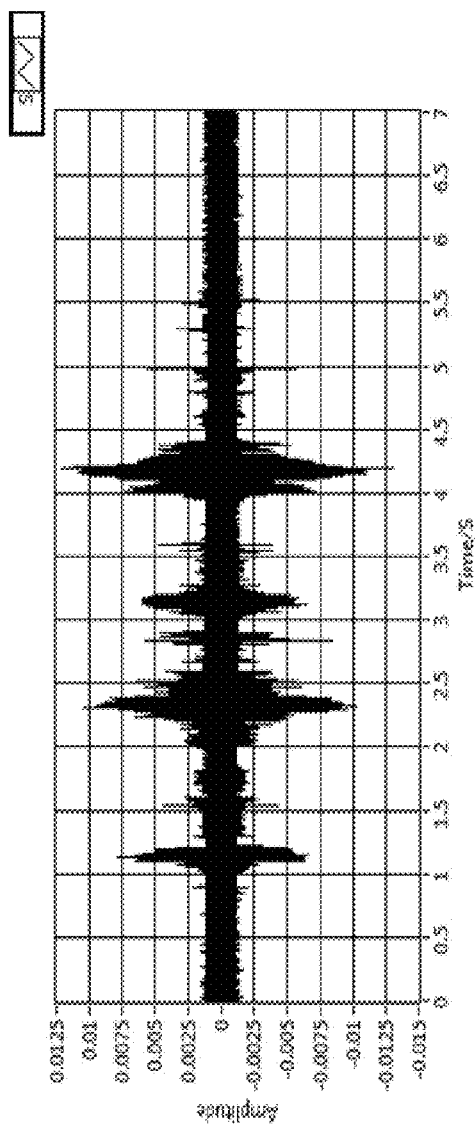
Figure 17:
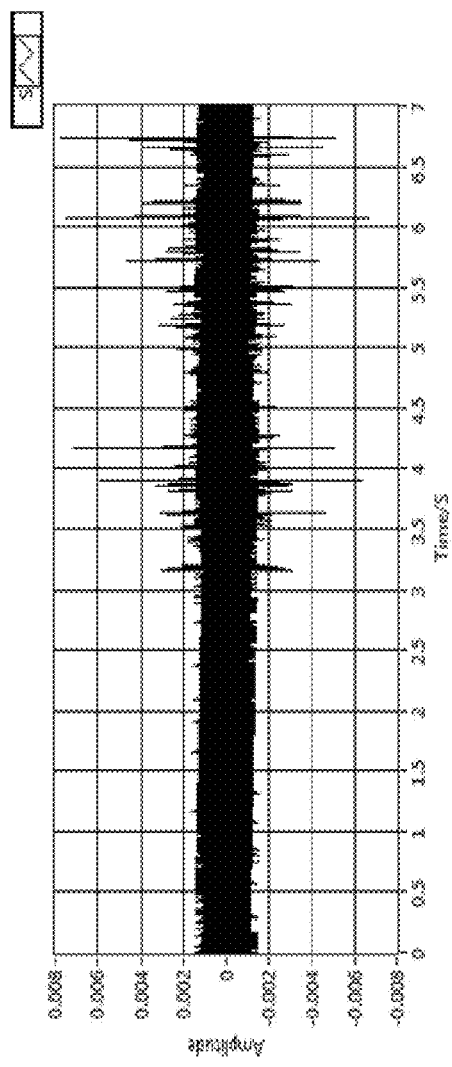

FIGS. 14-15 illustrate system responses to an input sine wave provided by actuator 41 during dynamic testing at a frequency of 149.9 kHz in with and without grease configurations. Notably, the without grease condition provided a very weak signal whereas the grease condition provided a strong signal. FIGS. 16-17 illustrate acoustic emission passive sensing of the same gate-valve seat interface. Notably, without grease condition provided an extremely noisy signal response. In contrast, the with-grease condition provided a reasonably quiet level of noise.

These above described exemplary plots illustrate how the various signatures can be used to determine the lubrication level and/or friction level. This could be accomplished over a continuum of levels related to different temperatures and gate-valve seat interface materials. Similar plots can be produced for a continuum of degradation levels and leakage rates for various temperatures and different materials utilized to construct the surfaces of the gate 33 and the valve seats 31, 32.

An embodiment of a computer-assisted method provides steps for monitoring health of a gate valve 20 is provided. The gate valve 20 can include a housing 21 having an internal cavity and a fluid passageway extending therethrough, a gate 33 and a valve seat 31, 32 contained within the housing 21 when operably employed. The gate 33 has a gate body 35 configured for slidable contact with the valve seat 31, 32. The one or more sensors 41, 43, 45, 47, 49 can be positioned adjacent to or in contact with the housing 21 of the gate valve 20. The one or more sensors 41, 43, 45, 47, 49 can include an acoustic emission sensor 47, 49, a vibration sensor 41, 43, 45, and/or a strain level sensing sensor 41, 43, 45.

The method includes the steps of: receiving sensor data including an acoustic emission signature, a vibration signature, and/or a strain level signature, representing one or more characteristics of an interface between surface portions of the gate body 35 and surface portions of the valve seat 31, 32 defining a gate-valve seat interface, the one or more characteristics comprising level of lubricity, level of friction, level of surface degradation, and/or leakage rate; and determining or identifying one or more of the following: the level of lubricity between the surface portions of the gate body 35 and the surface portions of the valve seat 31, 32, the level of friction between the surface portions of the gate body 35 and the surface portions of the valve seat 31, 32, the level of surface degradation of the surface portions of the gate body 35, the surface portions of the valve seat 31, 32, or both the surface portions of the gate body 35, and the surface portions of the valve seat 31, 32, and the leakage rate at the gate-valve seat interface.

The method can also include the steps of: receiving temperature data from a temperature sensor at 47, 49; and actuating an actuator 41, 43, 45 positioned on or in operable contact with an outer surface of the housing 21 of the gate valve 20 to generate an ultrasonic wave with a certain frequency. The operation of receiving can include receiving reflected or refracted portions of the ultrasonic wave emanating from the gate-valve interface. The operation of determining or identifying can include determining the level of surface degradation, to include detecting a certain change in wave intensity of the ultrasonic wave from that of a baseline intensity prior to substantial degradation occurring recorded at substantially the same temperature. Optionally, according to this configuration, the gate 33 can be maintained in a stationary position in relation to the valve seat 31, 32 when performing the steps of actuating and receiving, or the body 35 of the gate 33 can be sliding in contact with the valve seats 31, 32.

An embodiment of a method for monitoring health of a gate valve 20 includes the steps of: receiving an acoustic wave signal emitted by motion of a gate 33 of the gate valve 20, an ultrasonic wave signal comprising ultrasonic waves passing through the gate 33 of the gate valve 20, generated by an actuator 41, 43, 45 operable to emit ultrasonic waves through the gate 33 of the gate valve 20, or both the acoustic wave and the ultrasonic wave signals; and transmitting data measurements corresponding to the acoustic wave signal, the ultrasonic wave signal, or both the acoustic wave and the ultrasonic wave signals, respectively, to a data acquisition and analysis device 51.

According to an exemplary configuration, the gate valve 20 includes a valve seat 31, 32 and the gate 33 having a gate body 35 configured for slidable contact with the valve seat 31, 32, and the method can also include the steps of: connecting one or more sensors 41, 43, 45, 47, 49 to the gate valve 20, the one or more sensors 41, 43, 45, 47, 49 including an acoustic emission sensor 47, 49 operable to receive the acoustic wave signal emitted by motion of the gate 33 of the gate valve 20; and monitoring the data measurements received from a transmitter at 47, 49 during slidable movement between surface portions of the gate body 35 and surface portions of the valve seat 31, 32, for data representing an abnormal acoustic signal, the abnormal acoustic signal exceeding a normal signal threshold that is associated with normal operating conditions of the gate 33.

The method can also or alternatively include the steps of: connecting one or more sensors 41, 43, 45, 47, 49 to the gate valve 20, the one or more sensors 41, 43, 45, 47, 49 including an ultrasonic waves sensor 41, 43, 45 operable to receive the ultrasonic waves passing through the gate 33 of the gate valve 20; connecting the actuator 41, 43, 45 to the gate valve 20; actuating the actuator 41, 43, 45 when the gate 33 of the gate valve 20 is in a stationary position and in surface contact with valve seats 31, 32 to generate the ultrasonic waves; and monitoring the data measurements received from a transmitter at 47, 49 when the gate 33 of the gate valve 20 is in the stationary position and in surface contact with valve seats 31, 32, for data representing an abnormal ultrasonic wave signal, the abnormal ultrasonic wave signal exceeding a normal signal threshold that is associated with normal operating conditions of the gate 33.

The method can also or alternatively include the steps of: connecting one or more sensors to the gate valve, the one or more sensors 41, 43, 45, 47, 49 including both an acoustic emission sensor 47, 49 operable to receive the acoustic wave signal emitted by motion of the gate 33 of the gate valve 20, and an ultrasonic waves sensor 41, 43, 45 operable to receive the ultrasonic waves passing through the gate 33 of the gate valve 20. The steps can also include: connecting the actuator 41, 43, 45 to the gate valve 20; actuating the actuator 41, 43, 45 when the gate 33 of the gate valve 20 is in a stationary position and in surface contact with valve seats 31, 32 to generate the ultrasonic waves; monitoring the data measurements received from a transmitter at 47, 49 during slidable movement between surface portions of the gate body 35 and surface portions of the valve seat 31, 32, for data representing an abnormal acoustic signal, the abnormal acoustic signal exceeding a normal signal threshold that is associated with normal operating conditions of the gate 33; and monitoring the data measurements received from the transmitter when the gate 33 of the gate valve 20 is in the stationary position and in surface contact with valve seats 31, 32, for data representing an abnormal ultrasonic wave signal, the abnormal ultrasonic wave signal exceeding a normal signal threshold that is associated with normal operating conditions of the gate 33.

An embodiment of a method for monitoring health of a gate valve 20 includes the steps of: receiving an acoustic wave signal emitted by motion of a gate 33 of the gate valve 20; and transmitting data measurements corresponding to the acoustic wave signal to a data acquisition and analysis device 51 being operable to monitor the data measurements received from a transmitter at 47, 49, for data representing an abnormal acoustic wave signal.

An embodiment of a method for monitoring health of a gate valve 20 includes the steps of: actuating an actuator 41, 43, 45 connected to a gate valve 20 to emit ultrasonic waves through a gate 33 of the gate valve 20 when the gate 33 of the gate valve 20 is in a stationary position and in surface contact with valve seats 31, 32 of the gate valve 20; receiving the ultrasonic waves passing through the gate 33 of the gate valve 20 defining an ultrasonic wave signal when the gate 33 of the gate valve 20 is in the stationary position and in surface contact with the valve seats 31, 32 of the gate valve 20 and/or during slidable movement between surface portions of the gate 33 and surface portions of the valve seats 31, 32, and transmitting data measurements corresponding to the ultrasonic wave signal to a data acquisition and analysis device 51 being operable to monitor the data measurements received from a transmitter at 47, 49, for data representing an abnormal acoustic signal.

An embodiment of a system 30 for monitoring a gate valve 20 is provided. The system 30 includes one or more sensors 41, 43, 45, 47, 49 operably connected to a gate valve 20. The one or more sensors 41, 43, 45, 47, 49 is operable to receive one or more of the following: an acoustic wave signal emitted by motion of a gate 33 of the gate valve 20 and an ultrasonic wave signal comprising ultrasonic waves passing through the gate 33 of the gate valve 20. The ultrasonic waves generated by an actuator 41, 43, 45 are operable to emit ultrasonic waves through the gate 33 of the gate valve 20. The system 30 also includes a transmitter at 47, 49 operable to transmit data measurements corresponding to the acoustic wave signal, the ultrasonic wave signal, or both the acoustic wave and the ultrasonic wave signals, respectively, to a data acquisition and analysis device 51.

According to an exemplary configuration, the one or more sensors 41, 43, 45, 47, 49 include an acoustic emission sensor 47, 49 operable to receive the acoustic wave signal emitted by motion of the gate 33 of the gate valve 20; and the system 30 further comprises the data acquisition and analysis device 51 being operable to monitor the data measurements received from the transmitter for data representing an abnormal acoustic signal, the abnormal acoustic signal exceeding a normal signal threshold that is associated with normal operating conditions of the gate 33.

According to another exemplary configuration, the one or more sensors 41, 43, 45, 47, 49 include an ultrasonic waves sensor 41, 43, 45 operable to receive the ultrasonic waves passing through the gate 33 of the gate valve 20; and the system 30 further comprises the actuator 41, 43, 45 being operably connected to the gate valve 20, and the data acquisition and analysis device 51 being operable to monitor the data measurements received from the transmitter when the gate 33 of the gate valve 20 is in a stationary position and in surface contact with valve seats 31, 32, for data representing an abnormal ultrasonic wave signal, the abnormal ultrasonic wave signal exceeding a normal signal threshold that is associated with normal operating conditions of the gate 33.

Another embodiment of a gate valve 20 monitoring system 30 comprises: an acoustic emission sensor 47, 49 operably connected to a gate valve 20, the acoustic emission sensor 47, 49 operable to receive an acoustic wave signal emitted by motion of a gate 33 of the gate valve 20; a transmitter at 47, 49 operable to transmit data measurements corresponding to the acoustic wave signal to a data acquisition and analysis device 51; and the data acquisition and analysis device 51 being operable to monitor the data measurements received from the transmitter for data representing an abnormal acoustic wave signal defined as an acoustic wave signal exceeding a normal signal threshold that is associated with normal operating conditions of the gate 33.

Another embodiment of a gate valve 20 monitoring system 30 comprises: an actuator 41, 43, 45 operably connected to a gate valve 20, the actuator 41, 43, 45 operable to emit ultrasonic waves through a gate 33 of the gate valve 20; a sensor operably connected to the gate valve 20, the sensor operable to receive the ultrasonic waves passing through the gate 33 of the gate valve 20 defining an ultrasonic wave signal; a transmitter at 47, 49 operable to transmit data measurements corresponding to the ultrasonic wave signal to a data acquisition and analysis device 51; and the data acquisition and analysis device 51 being operable to monitor the data measurements received from the transmitter when the gate 33 of the gate valve 20 is in a stationary position and in surface contact with valve seats 31, 32 and/or during slidable movement between surface portions of the gate 33 and surface portions of the valve seats 31, 32, for data representing an abnormal ultrasonic wave signal defined as an ultrasonic wave signal exceeding a normal signal threshold that is associated with normal operating conditions of the gate 33.

Another embodiment of a gate valve 20 monitoring system 30 for monitoring a condition of a gate valve 20, comprises: a gate valve 20 including a housing 21 having an internal cavity and a fluid passageway extending therethrough, a gate 33 and a valve seat 31, 32 contained within the housing 21 when operably employed. The gate 33 has a gate body 35 configured for slidable contact with the valve seat 31, 32. The system 30 also includes one or more sensors 41, 43, 45, 47, 49 positioned adjacent to or in contact with an outer surface of the housing 21 of the gate valve 20. The one or more sensors 41, 43, 45, 47, 49 comprises one or more of the following: an acoustic emission sensor 47, 49, a vibration sensor 41, 43, 45, and a strain level sensing sensor 41, 43, 45. The system 30 also includes a logic module 51 configured to analyze one or more of the following: an acoustic emission signature, a vibration signature, and a strain level signature, representing one or more characteristics of an interface between surface portions of the gate body 35 and surface portions of the valve seat 31, 32 defining a gate-valve seat interface.

According to an exemplary configuration, the logic module 51 comprises non-transitory memory storing program code, and one or more processors for processing the program code, the program code comprising a set of instructions that when executed by the one or more processors, cause the one or more processors to perform the operations of: receiving sensor data including one or more of the following: an acoustic emission signature, a vibration signature, and a strain level signature, representing the one or more characteristics of the gate-valve seat interface, the one or more characteristics comprising one or more of the following: level of lubricity, level of friction, level of surface degradation, and leakage rate; and determining or identifying one or more of the following: the level of lubricity between the surface portions of the gate body 35 and the surface portions of the valve seat 31, 32, the level of friction between the surface portions of the gate body 35 and the surface portions of the valve seat 31, 32, the level of surface degradation of the surface portions of the gate body 35 and/or the surface portions of the valve seat 31, 32, and the leakage rate at the gate-valve seat interface.

According to the exemplary configuration, the operations further comprise: receiving temperature data from a temperature sensor at 47, 49; and actuating an actuator 41, 43, 45 positioned on or in operable contact with an outer surface of the housing 21 of the gate valve 20 to generate an ultrasonic wave with a certain frequency. The operation of receiving can include receiving reflected or refracted portions of the ultrasonic wave emanating from the gate-valve interface; and the operation of determining or identifying can include determining the level of surface degradation, to include detecting a certain change in wave intensity of the ultrasonic wave from that of a baseline intensity prior to substantial degradation occurring recorded at substantially the same temperature.

According to the exemplary configuration, the gate 33 can be maintained in a stationary position in relation to the valve seat 31, 32 when performing the operations of actuating and receiving, and when the data is being gathered. Alternatively, the actuating and receiving can be performed during movement of the body 35 of the gate 33 in contact with the valve seats 31, 32.

According to the exemplary configuration, the valve seat 31, 32 can include a sealing ring at 31, 32 positioned at a throat of a pipeline connector interface, and the operations can also or alternatively comprise: forming a continuum of signatures at different lubrication levels comprising one or more of the following: acoustic emission, vibration, and strain level signatures, defining a set of a corresponding plurality of lubrication level signature models; and comparing the received signature or signatures to a subset of the set of the lubrication level signature models to thereby determine the level of lubricity between the surface portions of the gate body 35 and the surface portions of the sealing ring. Optionally, the operation of forming a continuum of signatures at different lubrication levels can include forming a plurality of different sets of the lubrication level signature models for each of a corresponding plurality of different sealing ring materials, gate body materials, or both the sealing ring and the gate body materials utilized for constructing the sealing ring, the gate body 35, or both the sealing ring and the gate body 35, respectively. Also or alternatively, the operations can include identifying a need for addition of lubrication at the gate-valve interface.

According to this or another exemplary configuration, the valve seat 31, 32 comprises a sealing ring at 31, 32 positioned at a throat of a pipeline connector interface, and the operations also or alternatively comprise: forming a continuum of signatures at different degradation levels comprising one or more the following: acoustic emission, vibration, and strain level signatures, defining a set of a corresponding plurality of surface degradation level signature models; and comparing the received signature or signatures to a subset of the set of the surface degradation level signature models to thereby determine the level of degradation of surface portions of the sealing ring, the surface positions of the gate body 35, or both the surface portions the sealing ring and the surface portions of the gate body 35. The operations can also include identifying a need for replacing the seal ring.

Optionally, the operation of forming a continuum of signatures at different surface degradation levels can include forming a plurality of different sets of the surface degradation level signature models for each of a corresponding plurality of different sealing ring materials, gate body materials, or both the sealing ring and the gate body materials utilized for constructing the sealing ring, the gate body 35, or both the sealing ring and the gate body 35, respectively.

Optionally, the operation of forming a continuum of surface degradation level signature models can also or alternatively include associating each surface degradation level signature model of the continuum of surface degradation level signature models with a respective back pressure signature model for a respective valve actuator back pressure responsive to the back pressure encountered by a component of a valve actuator utilized to actuate the gate 33.

Optionally, the operation of determining a level of surface degradation can further or alternatively include sensing an acoustic emission, vibration, or strain level responsive to actuated movement of the gate valve 20 and measuring back pressure on the component of the gate valve 20 actuating system 30 associated therewith.

According to this or another exemplary configuration, the valve seat 31, 32 comprises a sealing ring at 31, 32 positioned at a throat of a pipeline connector interface, and the level of surface degradation comprises a level of surface wear of the surface portions of the valve seat 31, 32, the surface portions of the gate body 35, or both the surface portions of the valve seat 31, 32 and the surface portions of the gate body 35. In this configuration, the operations can also or alternatively comprise: forming a continuum of signatures at different surface wear levels comprising one or more of the following: acoustic emission, vibration, and strain level signatures defining a set of a corresponding plurality of surface wear level signature models; and comparing the received signature or signatures to a subset of the set of the surface wear level signature models to thereby determine the level of surface wear of the surface portions of the sealing ring, the surface portions of the gate body 35, or both the surface portions of the sealing ring and the surface portions of the gate body 35. The operations can also include identifying a need for replacing the seal ring. Optionally, the operation of forming a continuum of signatures at different surface wear levels can include forming a plurality of different sets of the surface wear level signature models for each of a corresponding plurality of different sealing ring materials, gate body materials, or both the sealing ring materials and the gate body materials utilized for constructing the sealing ring, the gate body 35, or both the sealing ring and the gate body 35, respectively.

According to this or another exemplary configuration, the valve seat 31, 32 comprises a sealing ring at 31, 32 positioned at a throat of a pipeline connector interface, and the level of surface degradation comprises a level of particulate matter buildup on the surface portions of the valve seat 31, 32, the surface portions of the gate body 35, or both the surface portions of the valve seat 31, 32 and the surface portions of the gate body 35. According to this configuration, the operations can also or alternatively comprise: forming a continuum of signatures at different particulate matter buildup levels comprising one or more of the following: acoustic emission, vibration, and strain level signatures defining a set of a corresponding plurality of particulate matter buildup level signature models; and comparing the received signature or signatures to a subset of the set of particulate matter buildup level signature models to thereby determine the level of particulate matter buildup on the surface portions of the sealing ring, the surface portions of the gate body 35, or both the surface portions of the sealing ring and the surface portions of the gate body 35, respectively.

Optionally, according to this configuration, the operation of forming a continuum of signatures at different particulate matter buildup levels can include forming a plurality of different sets of the particulate matter buildup level signature models for each of a corresponding plurality of different sealing ring materials, gate body materials, or the sealing ring materials and the gate body materials utilized for constructing the sealing ring, the gate body 35, or both the sealing ring and the gate body 35 respectively. Also or alternatively, the operations can include identifying a need for replacing the sealing ring, scraping the particulate matter from the surface portions of the gate body 35, or replacing the sealing ring and scraping the particulate matter from the surface portions of the gate body 35.

According to this or another exemplary configuration, the valve seat 31, 32 comprises a sealing ring at 31, 32 positioned at a throat of a pipeline connector interface, and the operations further comprise: forming a continuum of signatures at different leakage rates comprising one or more of the following: acoustic emission, vibration, and strain level signatures defining a set of a corresponding plurality of leakage rate signature models; and comparing the received signature or signatures to a subset of the set of leakage rate signature models to thereby determine the rate of leakage at the gate-valve interface. Optionally, the operation of forming a continuum of signatures at different lubrication levels can include forming a plurality of different sets of the leakage rate signature models for each of a corresponding plurality of different sealing ring materials, gate body materials, or both the sealing ring materials and the gate body materials utilized for constructing the sealing ring, the gate body 35, or both the sealing ring and the gate body 35, respectively. The operations can also or alternatively include identifying a need for replacing the sealing ring.

According to this or another exemplary configuration, the valve seat 31, 32 comprises a sealing ring at 31, 32 positioned at a throat of a pipeline connector interface, and the operations further comprise: forming a continuum of signatures at different friction levels between the surface portions of the gate 33 and the surface portions of the sealing ring in contact therewith during actuated movement of the gate comprising one or more of the following: acoustic emission, vibration, and strain level signatures defining a set of a corresponding plurality of friction level signature models; and comparing the received signature or signatures to a subset of the set of friction level signature models to thereby determine the level of friction between the surface portions of the gate body 35 and surface portions of the sealing ring. Optionally, the operation of forming a continuum of signatures at different friction levels can include forming a plurality of different sets of the friction level signature models for each of a corresponding plurality of different sealing ring materials, gate body materials, or both sealing ring materials and gate body materials utilized for constructing the sealing ring, the gate body 35, or both of the sealing ring and the gate body 35, respectively.

According to this or another exemplary configuration, the operations comprise predicting a gate-valve seat interface failure to include forming a plurality of different sets of gate-valve seat failure signature models for a corresponding plurality of different valve seat materials, valve body materials, or both valve seat materials and valve body materials.

According to the above described embodiment of a gate valve 20 monitoring system 30, the system 30 can be configured according to one or more or all of the above featured exemplary configurations.

Various embodiments of the present invention provide several advantages. For example, various embodiments can provide for a specific internal to valve cavity pressure controlling gate to seat valve health diagnostic capability. Various embodiments can provide feedback which can be utilized to predict gate-valve seat interface failure, and warn of any abnormal behavior involving this critical interface. The feedback basis can include a passive sensing approach, an active sensing approach, or a combination thereof. In the active sensing mode, PZT actuators can generate ultrasonic waves with a certain frequency. PZT sensors and/or AE sensors can receive the wave. Any significant change in the target surface condition will result in a change of wave intensity. In the passive sensing mode, actuators are not needed to generate the signal. The PZT and/or AE sensors receive the wave signal when the gate moves up and down in slidable contact with the valve seat. When faced with obstacles such as surface damage, or as a result of leaking, the system will receive an abnormal acoustic and/or vibratory signal.

According to various embodiments, active and/or passive sensors are placed internal and/or external to the gate valve cavity. In the active sensing mode, an ultrasonic wave of a certain frequency is generated by an actuator. This wave propagates along the sealing interface between the valve seat and valve gate. Any abnormalities or changes in wear characteristics of this interface can be recorded and transferred via a wired or wireless communication to a logic pod or other module for interpretation. In the passive sensing mode (listening mode), the movement the gate transfers a wave signal via wired or wireless communication to a logic pod or other module for interpretation. Any surface wear or damage will be picked up in this sensing mode. The passive sensing mode can enable additional corroborating data to be obtained regarding valve health, as well. Data providing for leak detection as well as data for quantifying the leakage rate at the gate-valve seat can be provided as well. Data related to the level of lubricity that exists on the gate-valve seat interface can be retrieved both during the passive and active sensing mode, as well. Various embodiments can provide for actively discerning levels of lubricant available to the gate-valve seat interface. Various embodiments allow users to interactively understand and quantify the exact sealability of the gate-valve seat interface.

Various embodiments compliment and advance the subsea and surface smart valve market. The information and feed back to a controller logic panel can allow operators/service providers to efficiently plan maintenance cycles, obtain interactive status updates of valve bore sealing mechanism, sealability and wear, as well as efficiency of lubrication acting in areas of high friction. In addition, back pressure feedback can be combined with this feedback specific information to allow users to more clearly understand data related to the health of the actuator itself. Various embodiments can facilitate much rig time savings in providing end users the ability to perform required regulatory validation tests interactive.

The present application is a non-provisional of and claims priority to and the benefit of U.S. Provisional Patent Application No. 61/746,693, titled Gate Valve Time Health Monitoring System, Apparatus, Program Code, and Related Methods, filed on Dec. 28, 2012, each incorporated herein by reference in its entirety.

In the drawings and specification, there have been disclosed a typical preferred embodiment of the technique, and although specific terms are employed, the terms are used in a descriptive sense only and not for purposes of limitation. The technique has been described in considerable detail with specific reference to these illustrated embodiments. It will be apparent, however, that various modifications and changes can be made within the spirit and scope of the technique as described in the foregoing specification and as set forth in the following claims. For example, although described primarily with respect to gate valves, one of ordinary skill in the art would recognize the applicability to various other types of valves which involve valve surfaces in slidable contact with each other. Further, although primarily described as being positioned on or adjacent an outer surface of the housing of the gate valve, one of ordinary skill in the art would recognize that positioning the various sensors within the cavity of the housing or on or adjacent an interior outer surface of the valve actuating mechanism is within the scope of the present invention. Still further, although the use of lead-zirconate-titanate (PZT) sensors/actuators, one of ordinary skill in the art would recognize that certain other solid-state sensors/actuators having comparable functionality are within the scope of the present invention.

That claimed is:

1. A gate valve monitoring system for monitoring a condition of a gate valve, comprising:
    a gate valve including a housing having an internal cavity and a fluid passageway extending therethrough, and a gate and a valve seat contained within the housing when operably employed, the gate having a gate body configured for slidable contact with the valve seat;
    one or more sensors positioned adjacent to or in contact with an outer surface of the housing of the gate valve, the one or more sensors comprising one or more of the following: an acoustic emission sensor, a vibration sensor, and a strain level sensing sensor; and
    a logic module configured to analyze one or more of the following: an acoustic emission signature, a vibration signature, and a strain level signature, representing one or more characteristics of an interface between surface portions of the gate body and surface portions of the valve seat defining a gate-valve seat interface,
    wherein the logic module comprises non-transitory memory storing program code, and one or more processors for processing the program code, the program code comprising a set of instructions that when executed by the one or more processors, cause the one or more processors to performed the operations of:
    receiving sensor data including one or more of the following: the acoustic emission signature, the vibration signature, and the strain level signature, representing the one or more characteristics of the gate-valve seat interface, the one or more characteristics comprising one or more the following: level of lubricity, level of friction, level of surface degradation, and leakage rate; and
    determining or identifying one or more of the following: the level of lubricity between the surface portions of the gate body and the surface portions of the valve seat, the level of friction between the surface portions of the gate body and the surface portions of the valve seat, the level of surface degradation of the surface portions of the gate body, the surface portions of the valve seat, or both the surface portions of the gate body, and the surface portions of the valve seat, and the leakage rate at the gate-valve seat interface,
    wherein the operations further comprise: forming a continuum of signatures at different characteristic levels comprising one or more the following: acoustic emission, vibration, and strain level signatures, each of the signatures defining a set of corresponding plurality of characteristic level signature models; and comparing the received signature or signatures to a subset of the set of the characteristic level signature models to thereby determine the level of the characteristic, and
    wherein the operation of forming a continuum of characteristic level signature models comprises: associating each characteristic level signature model of the continuum of characteristic level signature models with a respective back pressure signature model for a respective valve actuator back pressure responsive to the back pressure encountered by a component of a valve actuator utilized to actuate the gate.

2. A gate valve monitoring system as defined in claim 1, wherein the operations further comprise:
    receiving temperature data from a temperature sensor; and
    actuating an actuator positioned on or in operable contact with an outer surface of the housing of the gate valve to generate an ultrasonic wave with a certain frequency;
    wherein the operation of receiving includes receiving reflected or refracted portions of the ultrasonic wave emanating from the gate-valve interface; and
    wherein the operation of determining or identifying comprises determining the level of surface degradation, to include detecting a certain change in wave intensity of the ultrasonic wave from that of a baseline intensity prior to substantial degradation occurring recorded at substantially the same temperature.

3. A gate valve monitoring system as defined in claim 2, wherein the gate is maintained in a stationary position in relation to the valve seat when performing the operations of actuating and receiving.

4. A gate valve monitoring system as defined in claim 1, wherein the valve seat comprises a sealing ring positioned at a throat of a pipeline connector interface, and wherein the operations further comprise:
    when the one or more characteristics represented by the sensor data includes the level of lubricity, forming the continuum of signatures at different lubrication levels comprising one or more of the following: acoustic emission, vibration, and strain level signatures, defining the set of the plurality of signature models corresponding to the level of lubricity; and
    comparing the received signature or signatures to a subset of the set of the signature models corresponding to the level of lubricity to thereby determine the level of lubricity between the surface portions of the gate body and the surface portions of the sealing ring.

5. A gate valve monitoring system as defined in claim 4, wherein the operation of forming the continuum of signatures at different lubrication levels, includes:
    forming a plurality of different sets of the lubrication level signature models for each of a corresponding plurality of different sealing ring materials, gate body materials, or both the sealing ring and the gate body materials utilized for constructing the sealing ring, the gate body, or both the sealing ring and the gate body, respectively.

6. A gate valve monitoring system as defined in claim 4, wherein the operations further comprise:
    identifying a need for addition of lubrication at the gate-valve interface.

7. A gate valve monitoring system as defined in claim 1, wherein the valve seat comprises a sealing ring positioned at a throat of a pipeline connector interface, wherein the operations further comprise:
   when the one or more characteristics represented by the sensor data includes the level of surface degradation, forming the continuum of signatures at different degradation levels comprising one or more the following: acoustic emission, vibration, and strain level signatures, defining the set of the plurality of signature models corresponding to the level of surface degradation; and
   comparing the received signature or signatures to a subset of the set of the signature models corresponding to the level of surface degradation to thereby determine the level of degradation of surface portions of the sealing ring, the surface positions of the gate body, or both the surface portions the sealing ring and the surface portions of the gate body.

8. A gate valve monitoring system as defined in claim 7, wherein the operation of forming the continuum of signatures at different surface degradation levels, includes:
   forming a plurality of different sets of the surface degradation level signature models for each of a corresponding plurality of different sealing ring materials, gate body materials, or both the sealing ring and the gate body materials utilized for constructing the sealing ring, the gate body, or both the sealing ring and the gate body, respectively.

9. A gate valve monitoring system as defined in claim 7, wherein the operations further comprise:
   identifying a need for replacing the sealing ring.

10. A gate valve monitoring system as defined in claim 1, wherein the valve seat comprises a sealing ring positioned at a throat of a pipeline connector interface, wherein the level of surface degradation comprises a plurality of different levels of surface wear of the surface portions of the valve seat, the surface portions of the gate body, or both the surface portions of the valve seat and the surface portions of the gate body, and wherein the operations further comprise:
   forming the continuum of signatures at the plurality of different levels of surface wear comprising one or more of the following: acoustic emission, vibration, and strain level signatures defining a set of a corresponding plurality of different surface wear level signature models; and
   comparing the received signature or signatures to a subset of the set of the surface wear level signature models to thereby determine the level of surface wear of the surface portions of the sealing ring, the surface portions of the gate body, or both the surface portions of the sealing ring and the surface portions of the gate body.

11. A gate valve monitoring system as defined in claim 10, wherein the operation of forming the continuum of signatures at different surface wear levels, includes:
   forming a plurality of different sets of the surface wear level signature models for each of a corresponding plurality of different sealing ring materials, gate body materials, or both the sealing ring materials and the gate body materials utilized for constructing the sealing ring, the gate body, or both the sealing ring and the gate body, respectively.

12. A gate valve monitoring system as defined in claim 10, wherein the operations further comprise:
   identifying a need for replacing the sealing ring.

13. A gate valve monitoring system as defined in claim 1, wherein the valve seat comprises a sealing ring positioned at a throat of a pipeline connector interface, wherein the level of surface degradation comprises a plurality of different levels of particulate matter buildup on the surface portions of the valve seat, the surface portions of the gate body, or both the surface portions of the valve seat and the surface portions of the gate body, and wherein the operations further comprise:
   forming the continuum of signatures at the plurality of different levels of particulate matter buildup comprising one or more of the following: acoustic emission, vibration, and strain level signatures defining a set of a corresponding plurality of different particulate matter buildup level signature models; and
   comparing the received signature or signatures to a subset of the set of particulate matter buildup level signature models to thereby determine the level of particulate matter buildup on the surface portions of the sealing ring, the surface portions of the gate body, or both the surface portions of the sealing ring and the surface portions of the gate body, respectively.

14. A gate valve monitoring system as defined in claim 13, wherein the operation of forming the continuum of signatures at different particulate matter buildup levels, includes:
   forming a plurality of different sets of the particulate matter buildup level signature models for each of a corresponding plurality of different sealing ring materials, gate body materials, or the seal ring materials and the gate body materials utilized for constructing the sealing ring, the gate body, or both the seal ring and the gate body respectively.

15. A gate valve monitoring system as defined in claim 13, wherein the operations further comprise:
   identifying a need for replacing the sealing ring, scraping the particulate matter from the surface portions of the gate body, or replacing the seal ring and scraping the particulate matter from the surface portions of the gate body.

16. A gate valve monitoring system as defined in claim 1, wherein the valve seat comprises a sealing ring positioned at a throat of a pipeline connector interface, and wherein the operations further comprise:
   when the one or more characteristics represented by the sensor data includes leakage rate, forming the continuum of signatures at different leakage rates comprising one or more of the following: acoustic emission, vibration, and strain level signatures defining the set of the plurality of signature models corresponding to the leakage rate; and
   comparing the received signature or signatures to a subset of the set of the signature models corresponding to the leakage rate to thereby determine the rate of leakage at the gate-valve interface.

17. A gate valve monitoring system as defined in claim 16, wherein the operation of forming the continuum of signatures at different lubrication levels, includes:
   forming a plurality of different sets of the leakage rate signature models for each of a corresponding plurality of different sealing ring materials, gate body materials, or both the seal ring materials and the gate body materials utilized for constructing the sealing ring, the gate body, or both the seal ring and the gate body, respectively.

18. A gate valve monitoring system as defined in claim 16, wherein the operations further comprise:
   identifying a need for replacing the sealing ring.

19. A gate valve monitoring system as defined in claim 1, wherein the valve seat comprises a sealing ring positioned at a throat of a pipeline connector interface, and wherein the operations further comprise:

when the one or more characteristics represented by the sensor data includes the level of friction forming the continuum of signatures at different friction levels between the surface portions of the gate and the surface portions of the sealing ring in contact therewith during actuated movement of the gate comprising one or more of the following: acoustic emission, vibration, and strain level signatures defining the set of the plurality of signature models corresponding to the level of friction; and comparing the received signature or signatures to a subset of the set of the signature models corresponding to the level of friction to thereby determine the level of friction between the surface portions of the gate body and surface portions of the sealing ring.

20. A gate valve monitoring system as defined in claim 19, wherein the operation of forming the continuum of signatures at different friction levels, includes:

forming a plurality of different sets of the friction level signature models for each of a corresponding plurality of different sealing ring materials, gate body materials, or both seal ring materials and gate body materials utilized for constructing the sealing ring, the gate body, or both of the seal ring and the gate body, respectively.

21. A gate valve monitoring system as defined in claim 1, wherein the operations further comprise:

predicting a gate-valve seat interface failure, comprising:
forming a plurality of different sets of gate-valve seat failure signature models for a corresponding plurality of different valve seat materials, valve body materials, or both valve seat materials and valve body materials.

22. A gate valve monitoring system comprising:

an acoustic emission sensor operably connected to a gate valve, the acoustic emission sensor operable to receive an acoustic wave signal emitted by motion of a gate of the gate valve;

a transmitter operable to transmit data measurements corresponding to the acoustic wave signal to a data acquisition and analysis device; and the data acquisition and analysis device operable to monitor the data measurements received from the transmitter for data representing an abnormal acoustic wave signal, the abnormal acoustic wave signal exceeding a normal signal threshold that is associated with normal operating conditions of the gate, wherein the data acquisition and analysis device comprises non-transitory memory storing program code, and one or more processors for processing the program code, the program code comprising a set of instructions that when executed by the one or more processors, cause the one or more processors to perform the operations of:

receiving the acoustic emission sensor data representing one or more characteristics of a gate-valve seat interface, the one or more characteristics comprising one or more the following: level of lubricity, level of friction, level of surface degradation, and leakage rate; and determining or identifying one or more of the following:
the level of lubricity between the surface portions of a gate body and surface portions of the valve seat,
the level of friction between the surface portions of the gate body and the surface portions of the valve seat,
the level of surface degradation of the surface portions of the gate body, the surface portions of the valve seat, or both the surface portions of the gate body and the surface portions of the valve seat, and
the leakage rate at the gate-valve seat interface, wherein the operations further comprise: forming a continuum of signatures at different characteristic levels comprising acoustic emission signatures defining a set of corresponding plurality of characteristic level signature models; and comparing the received signature or signatures to a subset of the set of the characteristic level signature models to thereby determine the level of the characteristic, and wherein the operation of forming a continuum of characteristic level signature models comprises: associating each characteristic level signature model of the continuum of characteristic level signature models with a respective back pressure signature model for a respective valve actuator back pressure responsive to the back pressure encountered by a component of a valve actuator utilized to actuate the gate.

23. A gate valve monitoring system comprising:

an actuator operably connected to a gate valve, the actuator operable to emit ultrasonic waves through a gate of the gate valve;

a sensor operably connected to the gate valve, the sensor operable to receive the ultrasonic waves passing through the gate of the gate valve defining an ultrasonic wave signal;

a transmitter operable to transmit data measurements corresponding to the ultrasonic wave signal to a data acquisition and analysis device; and the data acquisition and analysis device operable to monitor the data measurements received from the transmitter when the gate of the gate valve is in a stationary position and in surface contact with valve seats and/or during slidable movement between surface portions of the gate and surface portions of the valve seats, for data representing an abnormal ultrasonic wave signal, the abnormal ultrasonic wave signal exceeding a normal signal threshold that is associated with normal operating conditions of the gate, wherein the data acquisition and analysis device comprises non-transitory memory storing program code, and one or more processors for processing the program code the program code comprising a set of instructions that when executed by the one or more processors, cause the one or more processors to perform the operations of:

receiving sensor data including the ultrasonic wave signals representing one or more characteristics of the gate-valve seat interface, the one or more characteristics comprising one or more the following: level of lubricity, level of friction, level of surface degradation, and leakage rate; and determining or identifying one or more of the following:
the level of lubricity between the surface portions of the gate body and the surface portions of the valve seat,
the level of friction between the surface portions of the gate body and the surface portions of the valve seat,
the level of surface degradation of the surface portions of the gate body, the surface portions of the valve seat, or both the surface portions of the gate body, and the surface portions of the valve seat, and
the leakage rate at the gate-valve seat interface, wherein the operations further comprise: forming a continuum of signatures at different characteristic levels comprising the data measurements, defining a set of corresponding plurality of characteristic level signature models; and comparing the received signature or signatures to a subset of the set of the characteristic level signature models to thereby determine the level of the characteristic, and wherein the operation of forming a continuum of characteristic level signature models comprises: associating each characteristic level signature model of the continuum of characteristic level signature models with a respective back pressure signature model for a respective valve actuator back pressure responsive to the back pressure encountered by a component of a valve actuator utilized to actuate the gate.

\* \* \* \* \*